United States Patent [19]

Broad, Jr.

[11] Patent Number: 4,987,905

[45] Date of Patent: Jan. 29, 1991

[54] NO HANDS CONTRACEPTIVE DEVICE

[76] Inventor: Robert L. Broad, Jr., 2300 Brookwood Dr., SE, Decatur, Ala. 35601

[21] Appl. No.: 300,139

[22] Filed: Jan. 23, 1989

[51] Int. Cl.⁵ .............................................. A61F 6/04
[52] U.S. Cl. .................................. 128/844; 604/349; 206/69
[58] Field of Search ................... 206/69; 128/842, 844; 604/347–352

[56] References Cited

U.S. PATENT DOCUMENTS

| | | | |
|---|---|---|---|
| 2,332,857 | 10/1943 | Karg | 206/69 |
| 2,365,556 | 12/1944 | Karg | 128/844 |
| 3,018,484 | 1/1962 | Koehn | 128/844 X |
| 3,136,417 | 6/1964 | Clinch | 128/844 X |
| 3,144,976 | 8/1964 | Freshour | 206/484 X |
| 3,282,414 | 11/1966 | Penska | 128/844 X |
| 4,731,064 | 3/1988 | Heyden | 604/352 |
| 4,872,463 | 10/1989 | Nishizono | 128/844 |

FOREIGN PATENT DOCUMENTS

| | | | |
|---|---|---|---|
| 253001 | 7/1964 | Australia | 206/69 |
| 36015 | 1/1909 | Austria | 604/349 |
| 111720 | 12/1928 | Austria | 604/349 |
| 162728 | 9/1905 | Fed. Rep. of Germany | 604/349 |
| 927529 | 5/1955 | Fed. Rep. of Germany | 206/69 |
| 2410697 | 6/1974 | Fed. Rep. of Germany | |
| 8802624 | 4/1988 | World Int. Prop. O. | 604/349 |

Primary Examiner—Robert A. Hafer
Assistant Examiner—Kevin G. Rooney

[57] ABSTRACT

A contraceptive device wherein a condom having a rolled portion is positioned between a pair of sheets which are secured together around the edges thereof to form a package for the condom, the condom being provided with a pair of strips positioned on opposite sides of the condom and each having one end helically rolled into the rolled portion of the condom and the other end thereof extending toward and secured to the sheets at the edges thereof. The strips, which are pulled to unroll the condom, and the condom are provided with sufficient give that the package can be torn into two parts and the condom pulled out of the package without premature unrolling. A tear guide extends across the package at a position on the package coordinated with slack in the strips. Preferably, the strips have a width sufficient to cause the rolled portion of the condom to assume a generally elliptical configuration having a major and minor axes, with the strips extending from the rolled portion of the condom in directions lying between the directions of the axes.

24 Claims, 4 Drawing Sheets

PRIOR ART DEVICE

PRIOR ART DEVICE

NO HANDS CONTRACEPTIVE DEVICE

FIELD OF THE INVENTION

This invention relates to contraceptive devices.

PRIOR ART

Condoms are not only used to prevent conception but also serve another purpose in that they inhibit the spread of a number of sexually transmitted diseases.

Most of the condoms now on the market are purchased in a sealed packet and are liberally coated with a lubricant. The user tears open the packet, removes the condom and then, using his hands, unrolls the condom onto his penis. One disadvantage of this is that the user cannot avoid having a large part of the lubricant wind up on his hands, an undesirable situation. Also, lubricated condoms are very slippery. This makes them difficult to put on and causes the donning to take an excessive amount of time. These problems have existed for decades.

Further, if a person who is infected with Acquired Immune Deficiency Syndrome (AIDS) has a cut or open sore on his hand his use of a conventional condom may not substantially lessen the possibility that he will transmit the AIDS virus to his sexual partner. The reason for this is that it is impossible for him to put on a conventional condom without touching it with his hands, so that the AIDS virus from body fluids from the cut or sore can contaminate the condom when it is touched as it is being put on.

West German Offenlegungsschrift No. 2,410,697 discloses a condom into which is rolled a pair of strands or strips which are pulled to unroll the condom. Applicant has discovered a major problem which frequently occurs when this device is used in a certain manner.

SUMMARY OF THE INVENTION

A contraceptive device wherein a condom having a rolled portion is positioned between a pair of sheets which are secured together around the edges thereof to form a package for the condom, the condom being provided with a pair of strips positioned on opposite sides of the condom with each strip having one end helically rolled into the rolled portion of the condom and the other end extending toward and secured to the sheets at the edges thereof. The strips, which are pulled to unroll the condom, and the condom are provided with sufficient give that the package can be torn into two parts and the condom pulled out of the package without premature unrolling. A tear guide extends across the package at a position on the package coordinated with slack in the strips. Preferably, the strips have a width sufficient to cause the rolled portion of the condom to assume a generally elliptical configuration having major and minor axes, with the strips extending from the rolled portion of the condom in directions lying between the directions of the axes.

DETAILED DESCRIPTION OF THE INVENTION

Weat German Offenlegungsschrift No. 2,410,697 discloses a condom having a pair of strands or strips rolled into the condom, the strips being pulled to unroll the condom. It has been discovered that a major problem frequently occurs when this condom is lubricated and the device is enclosed in a package. When the device is removed from the package the condom tends to unroll slightly, even when the utmost care is taken. If the device is removed from the package by pulling the strips or strands, premature unrolling of the condom is almost inevitable. By "premature unrolling" we mean a slight unrolling of the condom prior to contact with the user's penis. This slight unrolling of the condom is itself not the problem.

Figure 1:
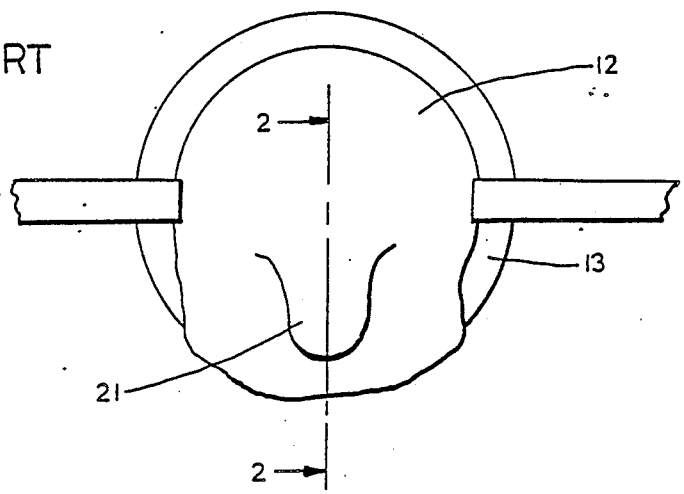
FIG. 1 is a plan view illustrating a problem frequently encountered when a prior art device is used in a certain manner.
Figure 2:
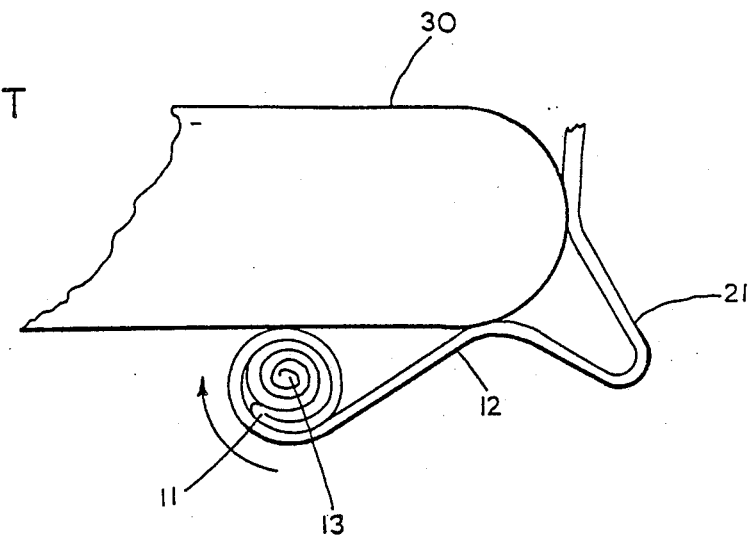
FIG. 2 is an enlarged fragmentary cross sectional view taken on line 2—2 of FIG. 1 further illustrating the problem prevented or solved by this invention, with portions of the device being greatly enlarged and crosshatching being omitted for clarity.

The problem that has been discovered, illustrated in FIGS. 1 and 2, is that when the condom unrolls prematurely, especially in the close confines of a package, the unrolled end of the condom tends, apparently because of the lubricant, to adhere to the rolled portion of the condom and then wrap around the rolled portion as it unrolls. This is best shown in FIG. 2, where a portion 11 of the unrolled end of the condom 12 has adhered to the rolled portion 13 and, as the rolled portion prematurely unrolled, has wrapped around and become rolled into the rolled portion 13. The condom is now tangled to the point that it cannot be unrolled further. It will tear before unrolling if additional force is applied to the strips. This problem, which occurs at a location between the strips, is prevented by the invention disclosed herein.

Figure 3:
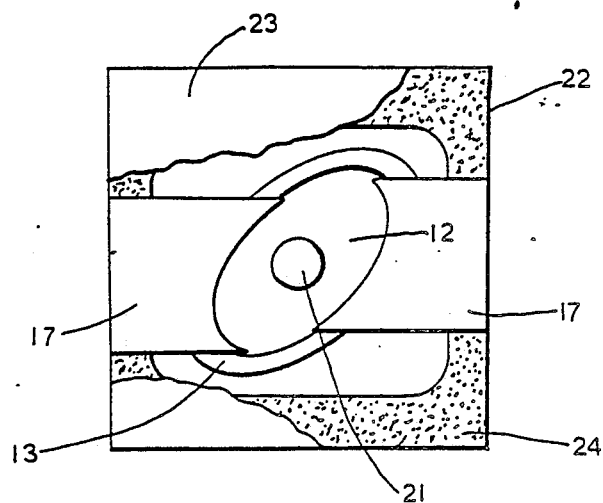
FIG. 3 is a plan view of the device of this invention with portions of the package broken away to show the elliptical configuration of the rolled portion of the condom and the directions in which the strips extend from the rolled condom.
Figure 4:
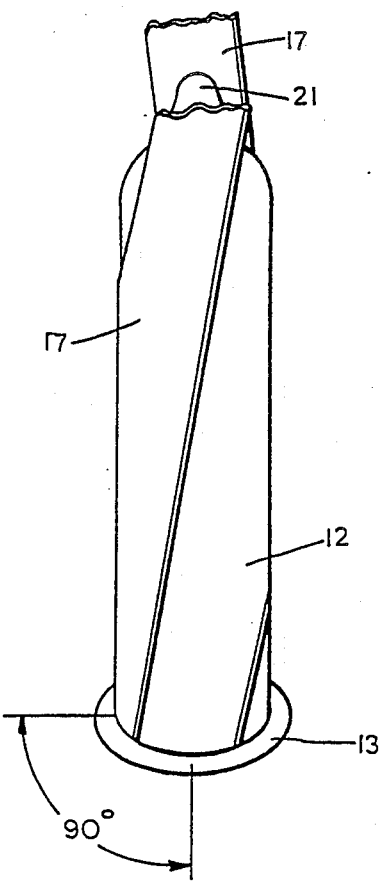
FIG. 4 is a side view showing the skewed positioning of the strips relative to the condom prior to rolling the condom.

Referring now in detail to FIGS. 3–8 of the drawings, there is shown a no hands contraceptive device made up of a condom 12 and a pair of strips 17 positioned on opposite sides of the condom, the condom being provided with a rolled portion 13 and a reservoir end 21. One end of each of the strips 17 is helically rolled into the rolled portion 20. The term "helically rolled" means that the strips 17 are positioned adjacent to the condom prior to rolling, as shown in FIG. 4, with each strip extending in a direction positioned at an angle to the direction of the axis of the condom. With the strips so positioned, the condom 16 is rolled to form the rolled portion 13.

The condom 12 is positioned between a pair of sheets 22 and 23 which are secured to each other around the edges thereof to form a hermetically sealed package for the condom 12, an area 24 extending around the periphery of the sheets 22 and 23 being stippled in FIG. 3 to indicate the portions of the sheets which are secured to each other. The free ends of the strips extend toward and are secured to the sheets 22 and 23 at the edges therof where the sheets are secured together. The sheets 22 and 23 may be made up of a layer of paper bonded to a layer of thermoplastic material such as polyethylene. If the sheets are positioned with the polyethylene layers in contact with each other, heat and presure applied to the edges of the sheets will seal them together.

Figure 9:
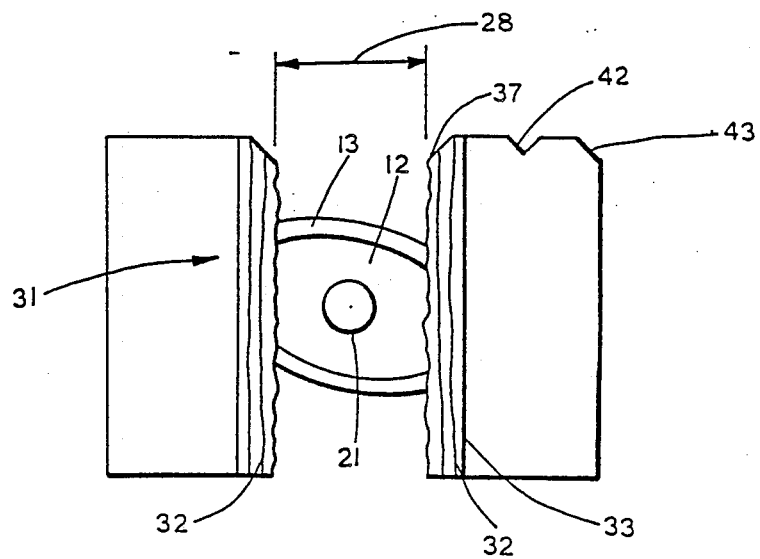
FIG. 9 is a plan view of the structure of FIG. 8 after the package has been torn into two parts and the condom pulled out of the package to an exposed position between the two parts.

To use the device, the user manually tears the package into two parts and then move the two parts away from each other to pull the condom out of the package to an "exposed" position between the two parts of the package, as shown in FIG. 9. At this point, the two parts of the package should be spaced apart a distance, indicated by reference numeral 28 in FIG. 9, equal to at least ¼th of the diameter of the circular portion 13 rolled without strips. Preferably, the condom is pulled to a "fully exposed" position between the two parts of the package, i.e., the entire condom is visible. The user then places the condom against the end of the penis 30 (FIG. 6) and, holding the severed parts of the package, pulls the strips 17. The condom will unroll onto the penis almost instantly without being touched by the user's hands.

In order to prevent premature unrolling of the rolled portion 13 as the condom is pulled from the package, it is essential that the device have sufficient give that the condom can be pulled to an exposed position without premature unrolling. By "give" we mean three things: slack in those portions of the strips 17 extending from the rolled portion 13 to the sealed area 24, a pivoting of the rolled portion 13 in the package when tension is applied to the strips 17 and the ability of the rolled portion 13 to elongate under tension without unrolling.

Figure 5:
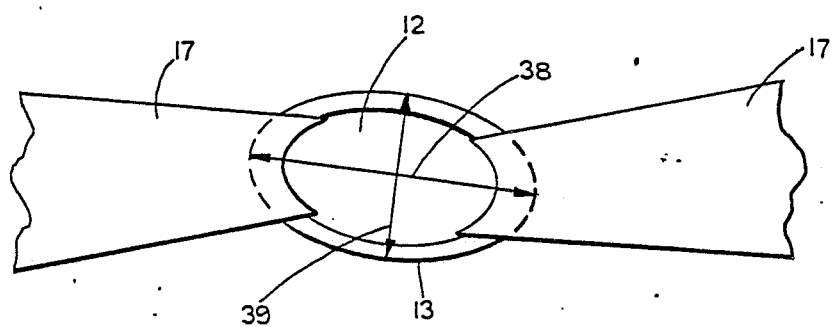
FIG. 5 is a plan view showing the position assumed by the rolled portion of the condom when a slight tension is applied to the strips.
Figure 6:
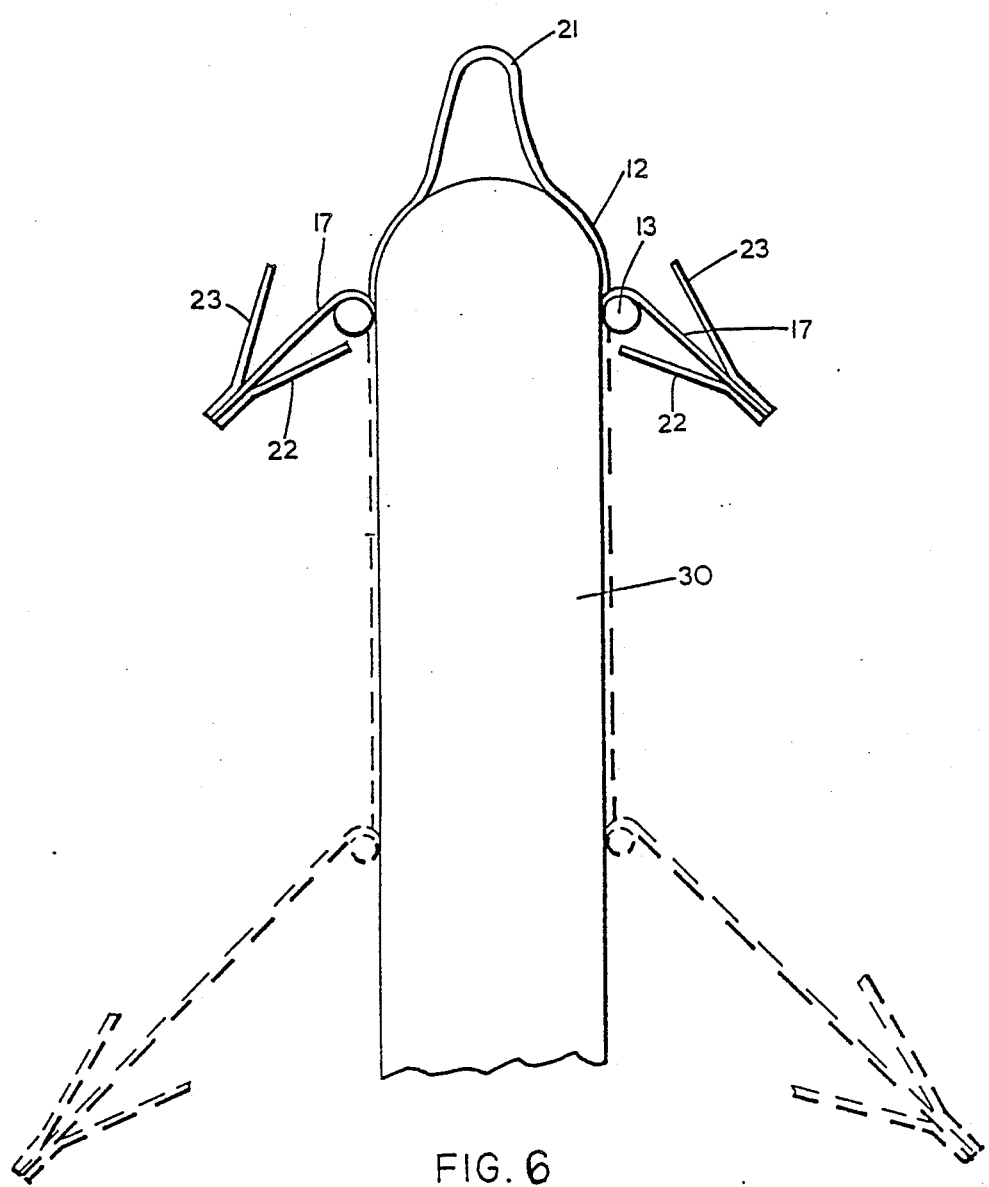
FIG. 6 is a schematic sectional view showing the manner in which the condom unrolls onto the user's penis when the strips are pulled, with crosshatching being omitted for clarity.
Figure 7:
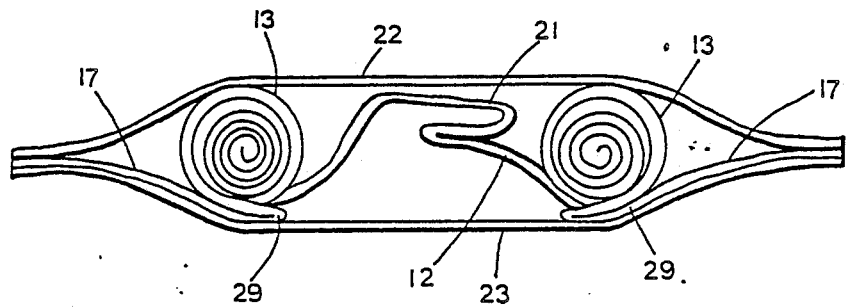
FIG. 7 is an enlarged cross sectional view of the contraceptive device showing the slack in the strips, with crosshatching being omitted for clarity.

The reference numeral 29 in FIG. 7 indicates the slack in the strips 17. When the generally elliptical rolled portion 13, described in greater detail below, is positioned in the package with the major axis of the rolled portion at an angle to the direction of the strips 17, as shown in FIG. 3, it will pivot under tension applied to the strips such that the major axis of the condom will substantially align itself with the strips 17, as shown in FIG. 5. This pivoting increases the distance between the ends of the elliptical rolled portion in the direction of the strips 17 to allow movement of the severed parts of the package away from each other. Also, the resistance of the rolled portion 13 to unrolling is sufficiently high that some elongation of the rolled portion under tension, without unrolling, is available. Each of these features contributes to the give which allows the severed parts of the package to be moved apart to expose the condom without premature unrolling. These features may be used individually or in combination to achieve the desired give.

The condom 12 is a conventional, commercially available item. The strips 17 may be made from a thin, flexible material which can be rolled into the condom. For example, a polymeric material such as polyethylene or other similar material may be used for making the strips 17. If the strips are cut from a polyethylene sheet or film it is preferred that the polyethylene not be highly oriented. Strips cut from softer, more easily stretched polyethylene appear to give better results. It is believed that these sheets or films are less oriented than harder films which require more force to be stretched. For example, strips cut from trash bags labelled "tall kitchen garbage bags" (believed to be less oriented polyethylene) are superior to strips cut from plastic bags (believed to be more oriented polyethylene) used at grocery store checkout counters for bagging groceries.

Figure 8:
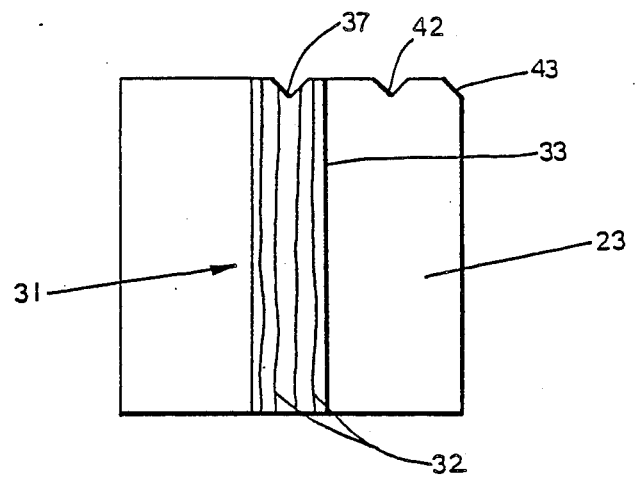
FIG. 8 is a plan view of the invention showing one embodiment of a tear guide positioned on the package to control the tear path when the package is opened.

Preferably, the package is provided with a tear guide 31 which extends across the package in a direction transverse to the direction in which the strips 17 extend (FIGS. 8 and 9). The purpose of the tear guide 31 is to control the path of tearing as the package is opened by manually tearing it into two parts. The tear guide is made up of a pair of boundaries which are spaced from each other to define a tear zone therebetween, with the boundaries confining the tearing to the tear zone. The boundaries may be in the form of strands 32 embedded in a tape 33 adhered to the package as shown in FIGS. 8 and 9 or they may be in the form of the edges of two spaced tapes adhered to the the package. A pair of spaced strands embedded in one of the sheets 22 or 23 may also be used as the tear guide.

The position of the tear guide 31 on the package is coordinated with the slack in the strips 17 in the package. For example, if it is desired to position the tear guide near one side of the package, then that strip 17 extending from the rolled portion 13 to the other side of the package is provided with a greater amount of slack to compensate for the fact that more slack is needed on that side to allow the condom to be pulled to an exposed position before the condom prematurely unrolls. If it is desired to position the tear guide 31 near the center of the package, the strips 17 should have about the same amount of slack, since each side of the condom will have to be pulled the same distance to reach an exposed position. In the preferred embodiment, the tear guide 31 is positioned near the center of the package so that, after the package is torn into two parts, the two parts will be about the same size.

The package is also provided with a stress raiser positioned in alignment with the tear guide. Preferably, the stress raiser is in the form of a notch 37 (FIG. 8) or slit in the edge of the sheets at a location in the tear zone, i.e., between the boundaries which define the tear zone. The use of the stress raiser facilitates the start of the tearing of the package at the desired location.

Preferably, the package is provided with an indicator which, in conjunction with the notch 37, can be used to determine the orientation of the package by touch without observing the package. The indicator is preferably in the form of an irregularity in the periphery of the package. This irregularity may be in the form of a second notch 42 (FIGS. 8 and 9) in the edge of the package or a clipped corner 43 of the package.

It is preferred that the strips 17 have widths sufficiently great to cause the rolled portion 13 of the condom to assume a generally elliptical configuration having a major axis 38 and a minor axis 39 (FIG. 5), with the widths of the strips being such that the length of the condom along the major axis is at least 1.2 times the width of the condom along the minor axis. More preferably, the strips will be of sufficient width to cause the length of the major axis 38 of the condom to be at least 1.4 times the length of the minor axis 39. It is most preferred that the major axis be at least 1.6 times the minor axis in length. The use of strips having such widths significantly increases the resistance of the condom to premature unrolling.

It is believed that the elliptical condom is more difficult to unroll because to unroll it will require significant tensile and compressive forces to be applied to the inner and outer portions of the more sharply bent ends of the condom. The use of strips having various widths and thicknesses is disclosed and claimed in copending application Ser. No. 300,140, filed Jan. 23, 1989 for "NO HANDS CONTRACEPTIVE DEVICE".

The ratio of the major axis length to minor axis length is determined primarily by the width of the strips 17. Thickness, and consequently the cross sectional area of the strips, will have some effect on this ratio, which might also be referred to as the condom length/width ratio. However, the range of thicknesses preferred for use is relatively small. Strips having a thickness of less than about 0.5 mils are more difficult to handle and manipulate while strips having a thickness greater than about 3.0 mils are more difficult to roll into the condom.

The thickness of the strips should be about 0.5 to about 3.0 mils, with the preferred strip thickness being about 0.7 to about 2.0 mils. However, in view of the fact that the useful thickness range is small and the fact that for any thickness a certain minimum width is required to achieve the desired major axis/minor axis ratio, the thickness of the strips can be more or less ignored provided the thickness is kept within a useful range. In this case, one would select a strip having a thickness within the most useful range, about 0.5 to 3.0 mils, and then make the strip of sufficient width to achieve the desired major axis/minor axis ratio.

The width of the strips 17 may also be expressed in terms of the length of the periphery or circumference of the rolled portion 13 of the condom 12. The sum of the widths of the strips 17 should be at least 20% of the length of the periphery of the rolled portion of the condom. Preferably, the sum of the widths of the strips is at least 30% of the periphery of the rolled portion of the condom and, most preferably, the sum of the widths of the strips is at least 40% of the length of such periphery. An easy way to determine the length of the circumference or periphery of the rolled portion 13 is to measure the diameter of the rolled portion, rolled without strips so that it is in its normal circular configuration, and then calculate the length of the circumference.

While the use of strips of the width described above increases the resistance of the condom to premature unrolling, the helical rolling of the strips 17 into the rolled portion of the condom provides a substantial improvement over the use of such strips alone. It is believed that this additional improvement is the result of the configuration of the elliptical condom and the positions assumed by the condom and the strips 17. This is best shown in FIG. 5, where the ends of the strips 17 assume positions such that the strips extend in directions which are less than 45 degrees from the direction of the major axis, this angle being measured in the plane of the rolled portion of the condom. Under a small amount of tension the condom pivots to a position where the major axis 38 extends substantially in the direction of the strips 17. It is believed that this is why larger forces can be applied to the strips to pull the condom out of the package without the risk of premature unrolling and tangling.

FIG. 4 shows the starting position used to helically roll the strips 17 into the condom 12. The strips are skewed or positioned at an angle to the axis of the condom before rolling. One way to characterize the angle at which the strips are rolled into the condom is to use the angle, which might be referred to as the skew angle, at which the strip extends around the periphery of the condom. In FIG. 4, the upper end of the strip 17 is displaced about ¼th of the way around the periphery of the condom from the lower end of the strip. This amounts to a skew angle of about 90 degrees, as indicated in FIG. 4. Preferably, the skew angle is at least 30 degrees and is most preferably at least 60 degrees.

EXAMPLE

Strips one inch in width cut from a 1.01 mil tall kitchen garbage bag were rolled into a condom both with and without skew. One of the strips was taped to the edge of a shelf and a small envelope was attached to the other strip by means of a paper clip. One cent coins were added, one at a time, to the envelope to apply a pulling force to the strips. The condom having the strips rolled without skew unrolled when 36 coins had been added to the envelope. The condom having the strips rolled with a skew angle of about 45 degrees had not begun to unroll when the paper clip tore out of the strip after 155 coins had been added to the envelope.

The above was repeated using strips one inch in width cut from a 1.5 mil polyethylene film. The condom having the strips rolled without skew unrolled when 20 coins had been added to the envelope. The condom with the strips rolled at a skew angle of about 45 degrees had not begun to unroll when the paper clip tore out of the strip after 213 coins had been added to the envelope.

It can readily be seen that the condom of this device can be put on in fraction of a second and the user's hands do not touch it. The conventional condom has neither of these advantages.

What is claimed is:

1. A contraceptive device, comprising
   a. a condom having a rolled portion,
   b. a pair of sheets positioned on opposite sides of the condom, said sheets being secured to each other around the edges thereof to form a package for the condom, and
   c. a pair of strips each having one end rolled into the rolled portion of the condom and the other end thereof extending toward and being secured to the sheets at opposite edges thereof, said rolled portion and strips having sufficient give that when the package is torn into two parts and the two parts moved away from each other the condom can be pulled out of the package to an exposed position between said two parts without premature unrolling.

2. The device of claim 1 wherein said give is sufficiently great that the condom can be pulled to a fully exposed position without premature unrolling.

3. The device of claim 1 wherein one of the sheets is provided with a tear guide extending across the sheet transversely to the direction in which the strips extend.

4. The device of claim 1 wherein the sum of the widths of the strips is at least 20% of the length of the periphery of the rolled portion of the condom to increase the resistance of the rolled portion to premature unrolling, said sum being determined by measuring the width of each strip at the widest part thereof and adding the widths.

5. The device of claim 3 wherein the tear guide extends across the a central portion of the package and the strips have generally the same amount of slack.

6. The device of claim 5 wherein the tear guide comprises a pair of spaced boundaries which form a tear zone therebetween.

7. The device of claim 6 wherein the boundaries are in the form of a pair of strands extending across the package.

8. The device of claim 6 wherein the sheets are provided with a stress raiser positioned at the edge of the sheets in alignment with the tear guide.

9. The device of claim 5 wherein the strips are helically rolled into the rolled portion of the condom at a skew angle of at least 5 degrees to increase the resistance of the rolled portion to premature unrolling.

10. The device of claim 9 wherein the strips are helically rolled into said rolled portion at a skew angle of at least 30 degrees.

11. A contraceptive device, comprising
 a. a condom having a roller portion,
 b. a pair of sheets positioned on opposite sides of the condom, said sheets being attached to each other around the edges thereof to form a package for the condom, and
 c. a pair of strips each having one end thereof rolled into the rolled portion of the condom and the other end thereof extending toward and being secured to the sheets at opposite edges thereof, said strips and said rolled portion having sufficient give that when the package is torn into two parts and the two parts moved away from each other the condom can be pulled out of the package to an exposed position between said two parts without premature unrolling, said strips being helically rolled into said rolled portion at a skew angle of at least 5 degrees to increase the resistance of the rolled portion to premature unrolling.

12. The device of claim 11 wherein the strips are helically rolled into said rolled portion at a skew angle of at least 30 degrees.

13. The device of claim 11 wherein the widths of the strips is sufficiently great to cause the rolled portion of the condom to assume a generally elliptical configuration having major and minor axes generally perpendicular to each other, said rolled portion retaining said elliptical configuration without the influence of outside forces, said strips being helically rolled at a skew angle such that said other ends of said strips extend from the condom in directions lying between the directions of said axes to increase the resistance of said rolled portion to premature unrolling.

14. The device of claim 11 wherein the sum of the widths of the strips is at least 20% of the length of the periphery of said rolled portion, said sum being determined by measuring each strip at the widest part thereof and adding the widths.

15. The device of claim 14 wherein the sum of the widths of said strips is at least 40% of the length of the periphery of the rolled portion of the condom.

16. The device of claim 13 wherein said other ends of said strips extend from the condom in directions which are less than 45 degrees from the direction of the major axis of the elliptical rolled portion.

17. The device of claim 13 wherein the strips extend substantially in the direction of said major axis.

18. A contraceptive device, comprising
 a. a condom having a rolled portion, and
 b. a pair of strips rolled into said rolled portion of the condom, said strips being helically rolled into said rolled portion at a skew angle of at least 5 degrees to increase the resistance of said rolled portion to premature unrolling.

19. The device of claim 18 wherein the strips are helically rolled into said rolled portion at a skew angle of at least 30 degrees.

20. The device of claim 18 wherein the widths of the strips are sufficiently great to cause the rolled portion of the condom to assume a generally elliptical configuration having a major axis and a minor axis, said rolled portion retaining said elliptical configuration without the influence of outside forces, said major axis having a length of at least 1.2 times the length of the minor axis to increase the resistance of the rolled portion to premature unrolling.

21. The device of claim 19 wherein the sum of the widths of the strips is at least 20% of the length of the periphery of the rolled portion of the condom, said sum being determined by measuring the width of each strip at the widest part thereof and adding the widths.

22. The device of claim 20 wherein the strips are helically rolled into the rolled portion of the condom at a skew angle such that the ends of the strips extend from said rolled portion in directions which are less than 45 degrees from the direction of the major axis.

23. The device of claim 22 wherein the ends of the strips extend from said rolled portion substantially in the direction of said major axis.

24. The device of claim 22 wherein the sum of the widths of the strips is at least 40% of the length of the periphery of the rolled portion and the skew angle is at least 60 degrees, said sum being determined by measuring the width of each strip at the widest part thereof and adding the widths.

* * * * *